US008559721B1

(12) United States Patent
Bartholomew

(10) Patent No.: US 8,559,721 B1
(45) Date of Patent: Oct. 15, 2013

(54) FILTER MOSAIC FOR DETECTION OF FUGITIVE EMISSIONS

(75) Inventor: Jarett Levi Bartholomew, Victor, NY (US)

(73) Assignee: Exelis, Inc., McLean, VA (US)

( * ) Notice: Subject to any disclaimer, the term of this patent is extended or adjusted under 35 U.S.C. 154(b) by 628 days.

(21) Appl. No.: 12/768,870

(22) Filed: Apr. 28, 2010

(51) Int. Cl.
G06K 9/00 (2006.01)
G01N 21/00 (2006.01)
G01J 5/02 (2006.01)

(52) U.S. Cl.
USPC ........... 382/181; 382/109; 356/436; 356/437; 356/438; 356/439; 250/339.13

(58) Field of Classification Search
USPC .......................................................... 382/303
See application file for complete search history.

(56) References Cited

U.S. PATENT DOCUMENTS

| | | | |
|---|---|---|---|
| 4,339,514 A * | 7/1982 | Biber ............................... 430/7 |
| 4,489,239 A * | 12/1984 | Grant et al. .............. 250/339.03 |
| 5,022,726 A * | 6/1991 | Austin et al. .................. 359/360 |
| 5,831,267 A * | 11/1998 | Jack et al. .................. 250/338.5 |
| 6,295,859 B1 * | 10/2001 | Hayden et al. ................. 73/23.2 |
| 6,690,472 B2 * | 2/2004 | Kulp et al. ..................... 356/437 |
| 6,995,846 B2 * | 2/2006 | Kalayeh et al. ............... 356/437 |
| 7,030,991 B1 * | 4/2006 | Kampe et al. ................. 356/454 |
| 7,161,678 B2 * | 1/2007 | Schultz ......................... 356/438 |
| 7,916,947 B2 * | 3/2011 | Conger et al. ................ 382/181 |
| 8,010,300 B1 * | 8/2011 | Stearns et al. .................. 702/24 |
| 8,121,798 B2 * | 2/2012 | Lippert et al. .................. 702/24 |
| 8,229,679 B1 * | 7/2012 | Matthews ....................... 702/24 |
| 8,269,971 B1 * | 9/2012 | Marsh et al. .................. 356/437 |
| 8,345,250 B1 * | 1/2013 | Janosky et al. ............... 356/437 |
| 2005/0064602 A1 * | 3/2005 | Kaufman et al. ............. 436/164 |
| 2008/0251724 A1 * | 10/2008 | Baliga et al. ............... 250/338.5 |
| 2009/0175530 A1 * | 7/2009 | Sjostrom et al. ............. 382/152 |
| 2009/0323181 A1 * | 12/2009 | Andrews et al. ............. 359/385 |

* cited by examiner

Primary Examiner — Michelle Entezari
(74) Attorney, Agent, or Firm — Ratnerprestia

(57) ABSTRACT

A method and apparatus for quantitative and qualitative imaging of fugitive emissions of gas, vapors, or fumes are described. The apparatus includes a filter mosaic for placement in registration over an imaging focal plane array (FPA). The filter mosaic includes at least two filter elements providing transmission response functions for transmitting wavelengths of light corresponding to an absorption wavelength (online wavelength) and a non-absorption wavelength (offline wavelength) of the targeted fugitive emission. Also described is an image processing method for transforming a filtered image into an image of the targeted fugitive emission.

9 Claims, 9 Drawing Sheets

FILTER MOSAIC FOR DETECTION OF FUGITIVE EMISSIONS

FIELD OF THE INVENTION

The present invention is related to a system and method for detecting fugitive emissions of fluid or gas in the atmosphere. More specifically, the present invention is related to remotely detecting fugitive emissions in the atmosphere using a combination of a filter mosaic and an imaging focal plane array.

BACKGROUND OF THE INVENTION

Remote sensing techniques are increasingly utilized in many fields including gas detection. More specifically, numerous chemical species detection techniques isolate and identify chemical species by exploiting unique spectral features. Many of these techniques use optical filters or include components that may be replaced by optical filters.

Some optical filter based remote sensing systems use a single focal plane array (FPA) with a rotating disk in front of the FPA that has multiple optical filters. To obtain a multispectral data set, one image is taken with each filter in the imaging path, while the filter wheel is rotated between imaging shots. This cumbersome approach is not acceptable in modern color photography and need not be acceptable in remote sensing situations.

Digital color photography is most commonly accomplished by using a Bayer filter superimposed on a focal plane array. The Bayer filter is an optical filtering array that includes three types of elements transmitting red, green, and blue light toward the FPA. The Bayer filter is placed in front of the FPA and aligned with the pixels of the FPA, such that each pixel may receive a filtered light transmitted through the Bayer filter.

As will be explained, remote sensing of a gas is accomplished by the present invention by using a filter mosaic that is registered, or aligned with the pixels of an FPA. Through proper alignment of the filter mosaic with the pixels of the FPA by the present invention, light arriving from a plume of the gas is filtered, detected and identified.

SUMMARY OF THE INVENTION

The present invention provides a system and method of detecting and measuring a path-integrated concentration of a fugitive gas. The path-integrated concentration is also referred to herein as a concentration path length (CPL) multiplied by a column length of the gas, expressed in parts per million (PPM) per meter.

The measurement is accomplished using a filter array superimposed in registration with a solid state imaging array. The filter array includes two or more filter elements arranged in a periodic pattern. The filter elements are chosen by the present invention to transmit predetermined wavelengths of light to the FPA for detection and identification of a gaseous emission.

The filter array includes at least two different filtering elements which allow at least one online wavelength (highly absorbing wavelength of the gas) and at least one offline wavelength (non-absorbing wavelength of the gas) to be transmitted to the FPA.

The filter array is configured to separate at least one online wavelength from at least one offline wavelength.

A processor is included for receiving the at least one online wavelength and the at least one offline wavelength from the filter array. The processor is configured to generate corresponding online data and offline data. The online data and offline data are generated from pixel intensities located in at least one sub-array of the imaging array.

The processor is also configured to interpolate among pixel intensities of the online and offline data generated from the at least one sub-array of the imaging array.

The processor is further configured to calculate a path integrated concentration of the target, defined as a concentration path length (CPL) of a gas emission from the target.

The target may include a species of gas. The received light may include two online wavelengths corresponding to two wavelengths absorbed by the species of gas. The received light may also include one offline wavelength corresponding to the one wavelength not absorbed by the species of gas. The two online and one offline wavelengths may be different from each other.

In another embodiment, the received light may include one online wavelength corresponding to the one wavelength absorbed by the species of gas, and two offline wavelengths corresponding to two wavelengths not absorbed by the species of gas. The one online and two offline wavelengths may be different from each other.

The filter array may include a silicon etalon with an antireflective coating deposited in a periodic pattern. The periodic pattern corresponds to a wavelength spacing between methane absorption features forming at least one online wavelength.

In yet another embodiment, the filter array may include a transparent substrate having dielectric coating layers deposited thereon. The dielectric coating layers form a transmission response curve coinciding with at least one online and at least one offline wavelengths.

In still another embodiment, the present invention includes a system for detecting a fugitive gas emission. The system includes a filter for filtering light from the gas emission including filtering an online wavelength and an offline wavelength, wherein the online wavelength corresponds to an absorption wavelength of the gas emission and the offline wavelength corresponds to a nonabsorption wavelength of the gas emission. An imager is included for receiving filtered light from the filter and outputting intensity data corresponding to the online and offline wavelengths. A processor is included for receiving the intensity data and calculating a concentration path length (CPL) based on the online and offline wavelengths. The CPL provides detection of the gas emission.

The filter includes an array of elements, one element providing the online wavelength filtering and another element providing the offline wavelength filtering. The imager includes an array of pixels. The array of elements of the filter is overlaid in registration with the array of pixels of the imager.

The CPL includes a ratio of online light to offline light from the gas emission after passing through the filter. The CPL also includes a calibration constant relating to a cross section of the gas emission.

A portion of the array of elements defining a sub-array of elements and a portion of the array of pixels defining a sub-array of pixels may be used, respectively, for filtering the light and outputting the intensity data.

The filter may include a transparent substrate having dielectric coating layers deposited thereon. The dielectric coating layers form a transmission response curve coinciding with the online and the offline wavelengths.

In yet another embodiment, the present invention is a method of identifying a plume of gas. The method includes the steps of:

filtering light received from the plume of gas, the filtered light including at least one online and at least one offline wavelengths corresponding, respectively, to at least one absorption wavelength and at least one nonabsorption wavelength of the plume of gas, transmitting the filtered light to an imager, outputting intensity data from the imager corresponding to the at least one absorption wavelength and the at least one nonabsorption wavelength of the plume of gas, and determining intensity levels of the at least one absorption wavelength and the at least one nonabsorption wavelength to identify the plume of gas.

The method may include the step of: transmitting a laser beam toward the plume of gas. The laser beam may include at least one online and at least one offline wavelengths.

Determining intensity levels includes computing a concentration path length (CPL) for the at least one absorption wavelength and the at least one nonabsorption wavelength.

BRIEF DESCRIPTION OF THE DRAWINGS

In the detailed description of embodiments of the present invention reference is made to the following figures.

DETAILED DESCRIPTION OF THE INVENTION

The following description is directed in particular to elements forming a part of or associated with the present invention. It is understood that elements not specifically shown in the figures or described may take various forms known to those skilled in the art.

Figure 1:
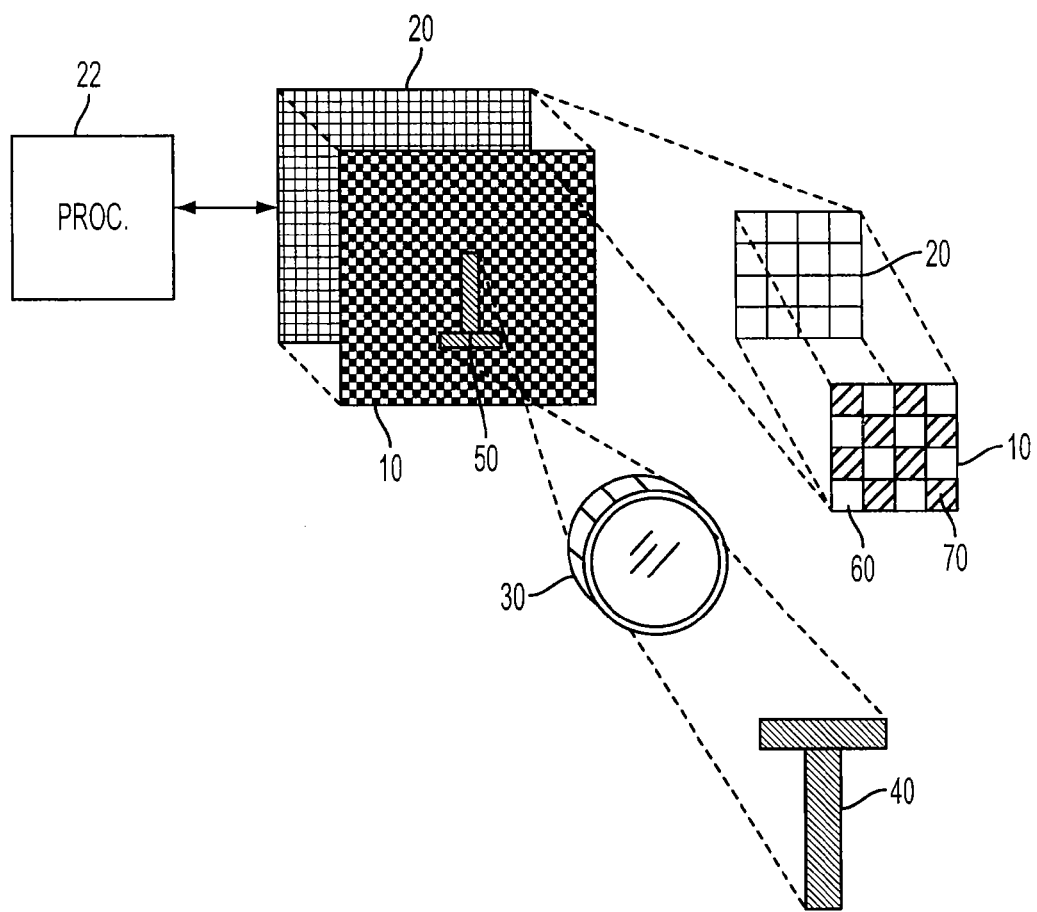
FIG. 1 is an exploded pictorial representation of the placement and registration of a periodic filter array with a focal plane imaging array.

FIG. 1 is an exploded view illustrating an embodiment of the present invention. As shown, an imaging system includes a focal plane array (FPA) 20 overlaid in registration (or aligned) with a filter array 10. The filter array 10 and imaging array 20 are used together with a lens 30 to form and record an image 50 of a target 40. A processor, generally designated as 22, is coupled to the imaging array for processing image intensity data outputted by the pixels of FPA 20.

Each filter element may be aligned to cover one or more pixels of the FPA. This is shown in a magnified view of a 4×4 pixel sub-array and a 4×4 filter mosaic sub-array of FPA 20 and mosaic filter array 10, respectively, in FIG. 1. One filter element is designated as 60 and another filter element is designated as 70. As shown, both filter elements are sequenced to form a checkerboard pattern, described further below.

Figure 2A:
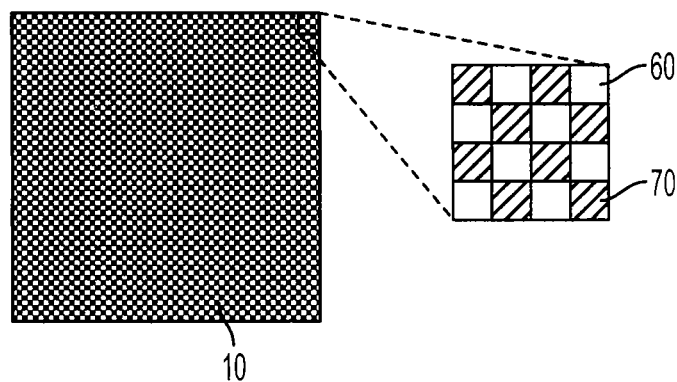
FIG. 2A is a pictorial representation of a periodic filter array including one element filter for transmitting light of a spectral region that is not absorbed by a target species and another element filter for transmitting light of a spectral region that is absorbed by the same target species.
Figure 4:
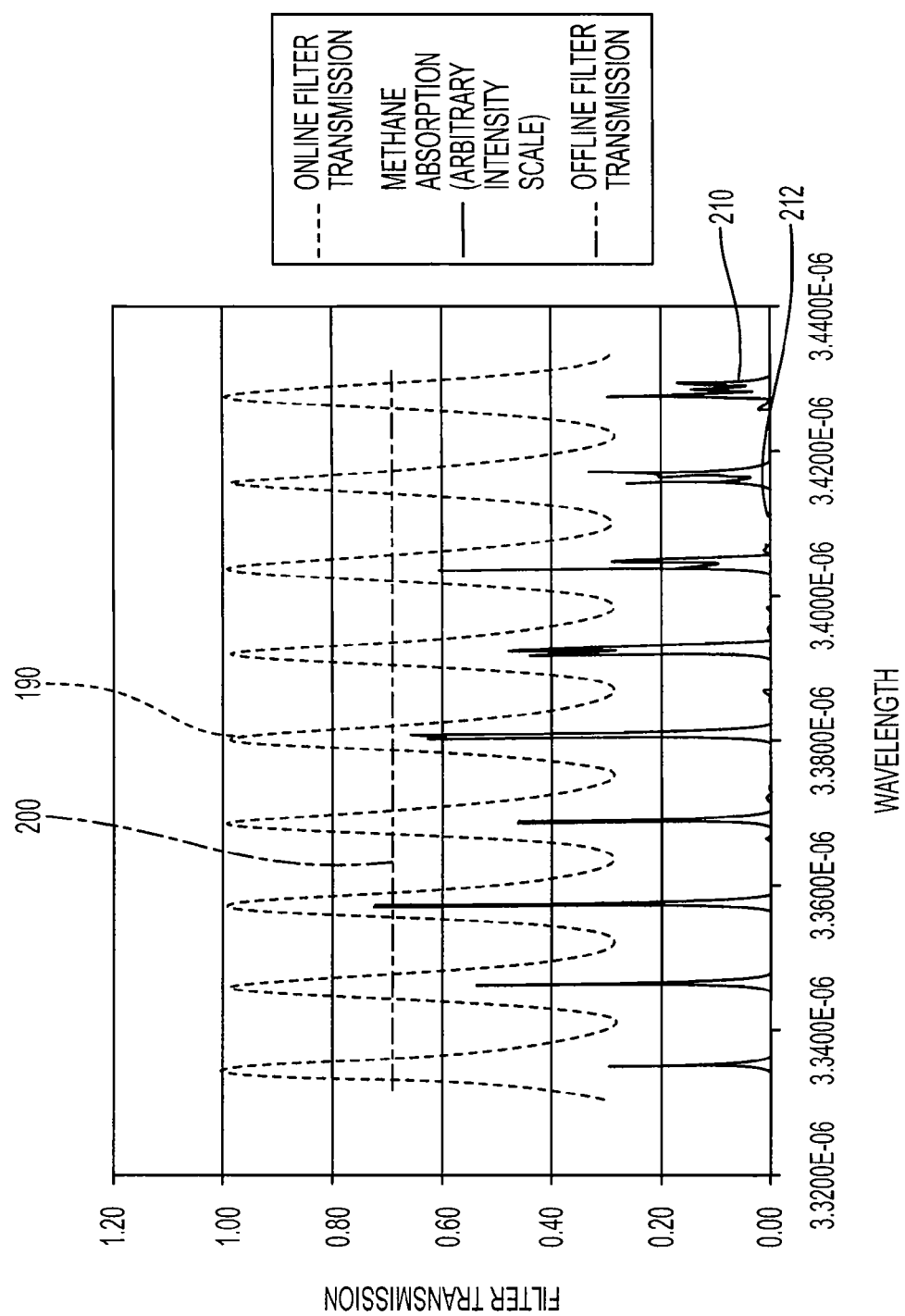
FIG. 4 is a plot of filter transmission versus wavelength showing examples of filter characteristics in a passive imaging system, in accordance with an embodiment of the present invention.

FIG. 2A illustrates one embodiment of a pattern designed into filter array 10 for detecting a single target gas, vapor, or other molecular species. The pattern illustrated includes a checkerboard pattern of two filter elements representing two spectral transmission functions. One filter element 70 exhibits a transmission function 190 (as shown in FIG. 4) designed to transmit wavelengths of light corresponding to one or multiple spectroscopic absorption features 210 (as shown in FIG. 4) of a target species. The absorption wavelengths are also referred to herein as online wavelengths 210.

The other filter element 60 exhibits a transmission function 200 (as shown in FIG. 4) designed to transmit wavelengths of light corresponding to non-absorption features 212 (as shown in FIG. 4) of a target species. The non-absorption wavelengths are also referred to herein as offline wavelengths 212.

Figure 2B:
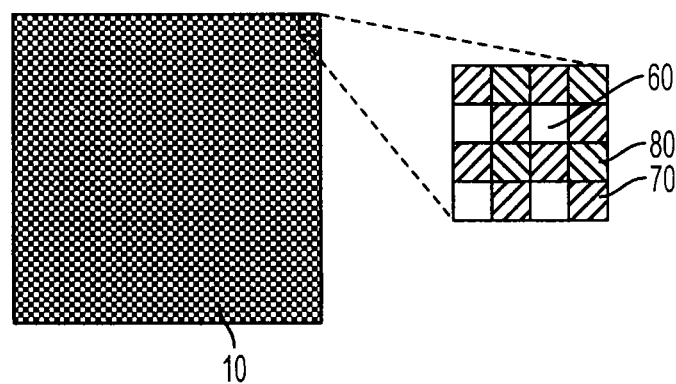
FIG. 2B is a pictorial representation of a periodic filter array including one element filter for transmitting light of a spectral region absorbed by a first target species, another element filter for transmitting light of a spectral region absorbed by a second target species, and a third element filter for transmitting light not absorbed by either target species.

FIG. 2B illustrates another embodiment of a filter array which expands the detection capability of the present invention to a second species. This is accomplished by adding a filter element 80 to the filter array. The filter element 80 includes a transmission function that corresponds to an absorption feature (online wavelength) of the second molecular species. Of course, the first molecular species is assumed to have online and offline wavelengths corresponding, respectively, to the transmission wavelengths of filter element 70 and filter element 60.

It will be appreciated that the filter configuration shown in FIG. 2B assumes that the two online wavelengths (one online wavelength for the first species and a different online wavelength for second species) are sufficiently close spectrally so as to allow the use of a single offline wavelength (one offline wavelength for both the first and second species). Furthermore, each of the two online wavelengths and the one offline wavelength are different from each other.

Figure 2C:
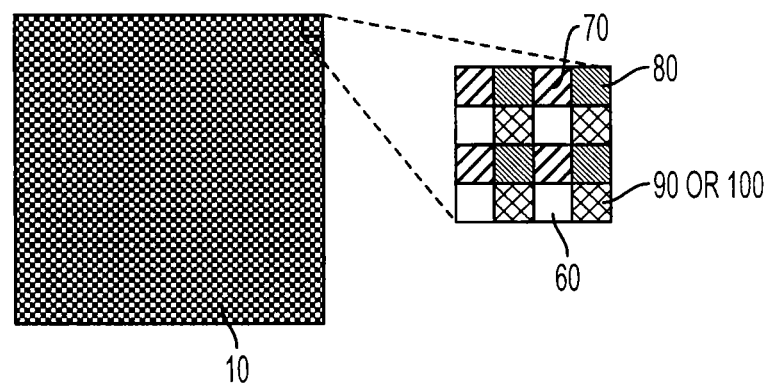
FIG. 2C is a pictorial representation of a periodic filter array including one element filter for transmitting light of a spectral region absorbed by a first target species, a second element filter for transmitting light of a spectral region absorbed by a second target species, a third element filter for transmitting light absorbed by a third target species or not absorbed by the first target species, and a fourth element filter not absorbed by any of the three target species or not absorbed by the second target species only.

FIG. 2C illustrates yet another embodiment of the filter mosaic of the present invention. As shown, the filter mosaic includes the addition of a fourth filter element to the three filter elements previously described with respect to the filter mosaic shown in FIG. 2B. The fourth filter element may be used to transmit a second offline wavelength 100, thereby independently detecting two molecular species (a first species includes first online and offline wavelengths and a second species includes second online and offline wavelengths, where the first and second species do not have a close spectral relationship).

Still referring to FIG. 2C, alternatively, the fourth filter element may be used to transmit a third online wavelength 90, thereby effectively detecting three molecular species in a close spectral region. Thus, for example, a first species includes first online and first offline wavelengths; a second species includes a second online and the first offline wavelength; and the third species includes a third online and the first offline wavelength, where the first, second and third species have a common first offline wavelength.

Figure 3:
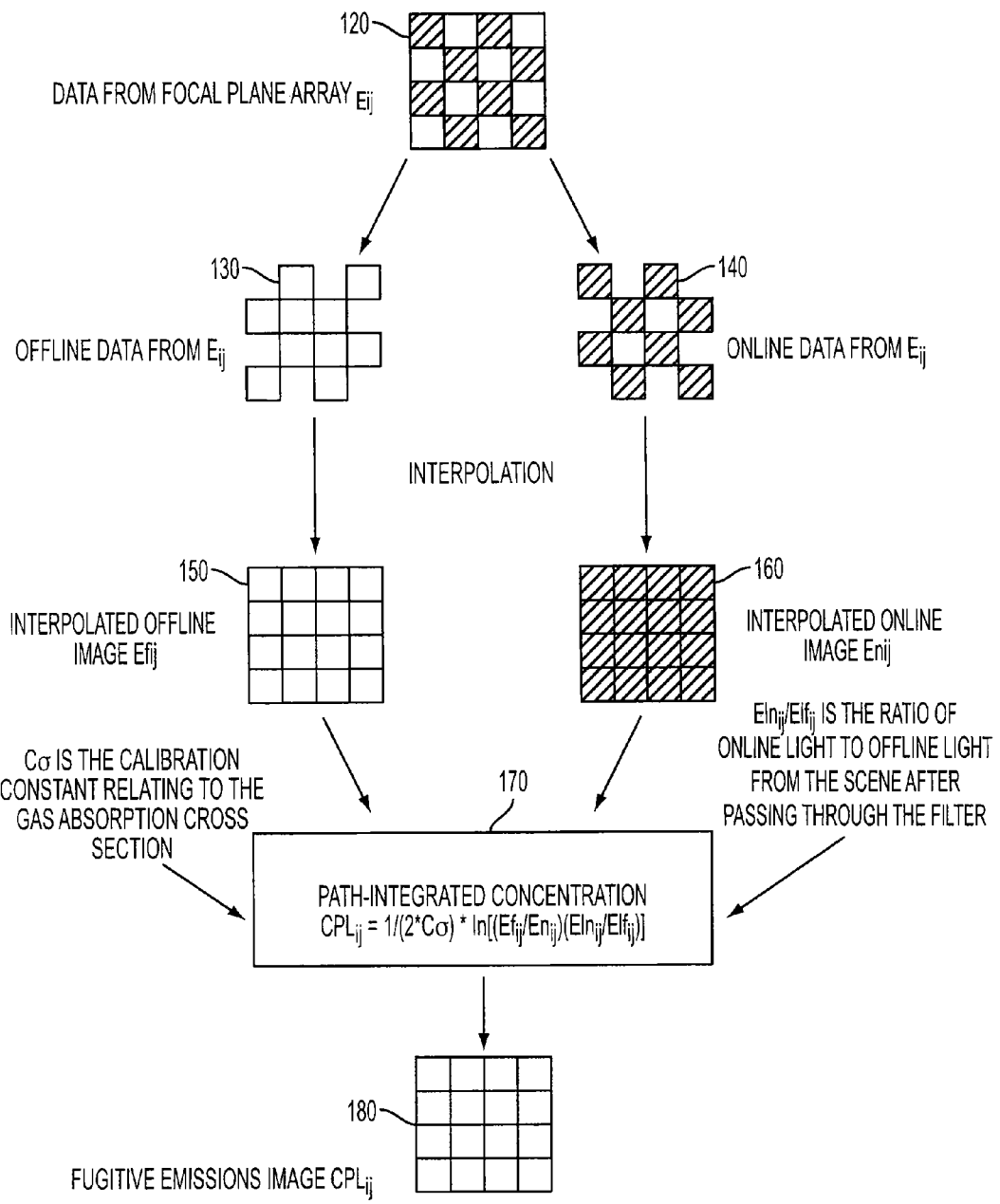
FIG. 3 is a diagrammatic representation of an image processing method for collecting data by a focal plane array overlaid with a filter mosaic array, and processing the data into a quantitative image of fugitive emissions, in accordance with an embodiment of the present invention.

FIG. 3 illustrates an image processing method in accordance with an embodiment of the present invention. As shown, the method transforms data acquired by a focal plane array, designated as 120, into an image of the target fugitive emission, designated as 180. In the first shown step, the data acquired by focal plane array 120 is divided into two separate data arrays, according to the type of filter transmission functions corresponding to the filter elements representing the online data 140 and the offline data 130. Each data array, next undergoes a two-dimensional interpolation to fill the pixel gaps left by separating the data arrays. The interpolated offline data 150 and online data 160 are then used to calculate a path-integrated concentration of the emission gas, designated as 170. The path integrated concentration, also referred to herein as the concentration path length (CPL) in ppm per m, is shown below by the following formula:

$$CPL_{ij} = 1/(2*C\sigma) * \ln[(Ef_{ij}/En_{ij})(EIn_{ij}/EIf_{ij})]$$

where:
the subscript ij refers to the coordinates of a particular pixel in the FPA;
$CPL_{ij}$ is the path-integrated concentration of the fugitive emission along the pixel line of sight from imaging array 20 to target 40 in FIG. 1;
$C\sigma$ is a calibration constant relating to the absorption cross section of the particular target species;
$Ef_{ij}$ (shown as 150 in FIG. 3) is the image of the target at the offline wavelength, after having been interpolated from the offline pixel set 130 in FPA 120;
$En_{ij}$ (shown as 160 in FIG. 3) is the image of the target at the online wavelength, after having been interpolated from the online pixel set 140 in FPA 120;
$EIn_{ij}$ relates to the illumination intensity of the scene at the online wavelength; and
$EIf_{ij}$ relates to the illumination intensity of the scene at the offline wavelength;

The ratio ($EIn_{ij}/EIf_{ij}$) may often be unity (1), depending on the choice of filter elements chosen and the spectral content of the illuminating light source.

Figure 6:
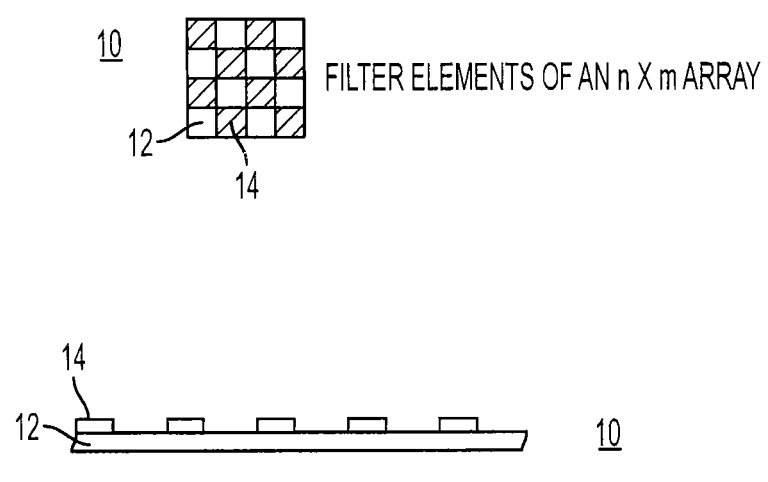
FIG. 6 is a top view and a sectional view of an exemplary filter array, in accordance with an embodiment of the present invention.

Referring now to FIGS. 4 and 6, there is shown an exemplary embodiment of a filter array of the present invention. As shown, filter array 10 includes a silicon etalon layer, designated as 12, having a thickness of 143 micrometers, with a free spectral range of 305+/−2 GHz. A first side of layer 12 has an anti-reflective (AR) coating deposited in a periodic pattern, designated as 14. The remainder surfaces on the first side and the entire second side of layer 12 remain uncoated. The uncoated surfaces of the silicon layer have high refractive index materials that naturally reflect a portion of the incident light, thereby forming reflective surfaces required to form an etalon.

The etalon regions (uncoated regions) of filter array 10 have a periodic spectral response, shown by curve 190. The spectral response has a frequency that matches the spectral response of methane absorption features, shown by spectral absorption peaks 210. The etalon regions form the online regions 70 of filter array 10. Temperature control of the etalon regions ensures that the transmission peaks shown in curve 190 remain aligned with the methane absorption peaks 210.

The coated regions of the filter array spoil the etalon, creating a flat spectral transmission response, shown by straight horizontal line 200. The flat spectral response forms offline elements 60 of filter array 10.

The filter characterized by FIGS. 4 and 6 is useful when illuminating the scene with a spectrally broad light source, such as the sun, a passive thermal radiator, an active thermal radiator, an incandescent lamp, a discharge lamp, or a fluorescent lamp.

Figure 5:
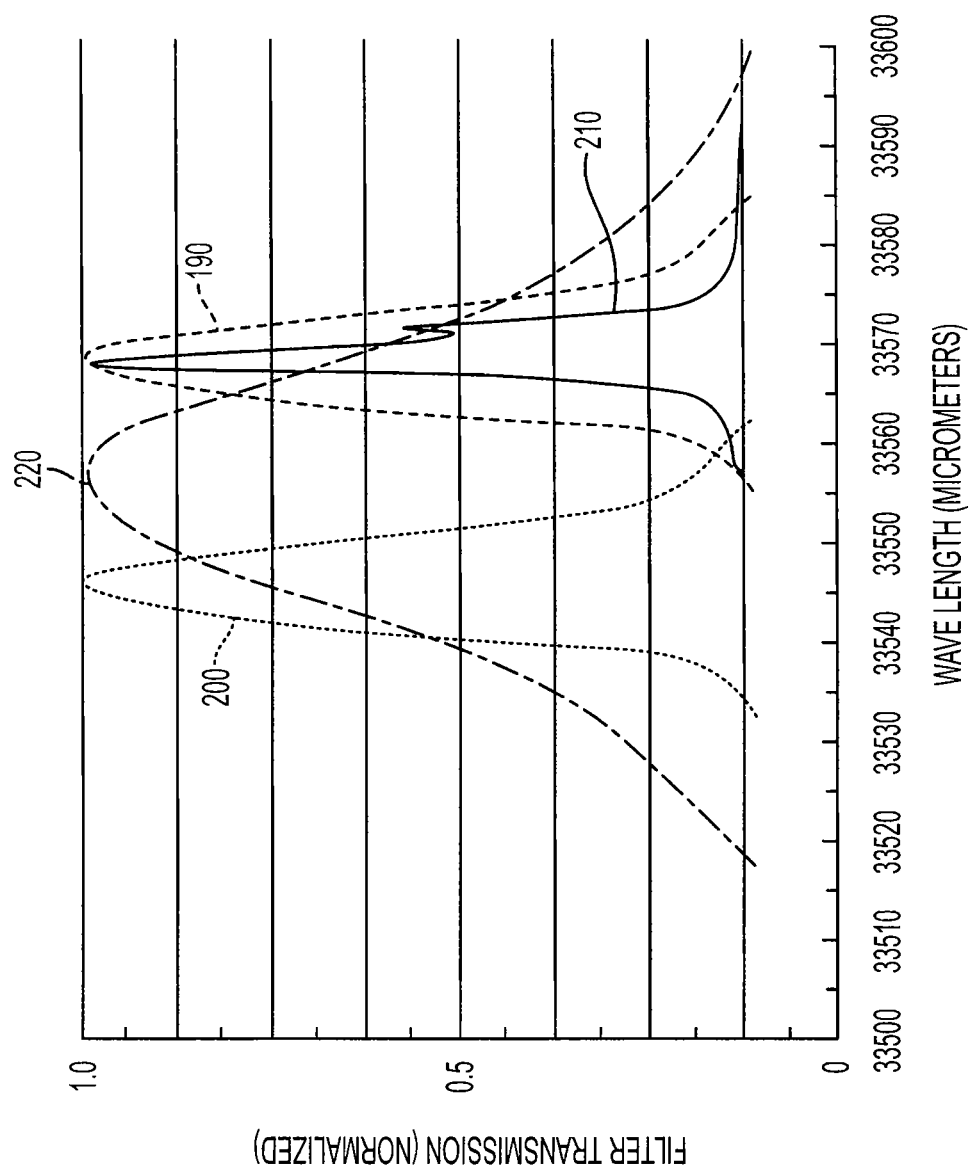
FIG. 5 is a plot of filter transmission versus wavelength showing examples of filter characteristics in an active imaging system, in accordance with an embodiment of the present invention.
Figure 7:
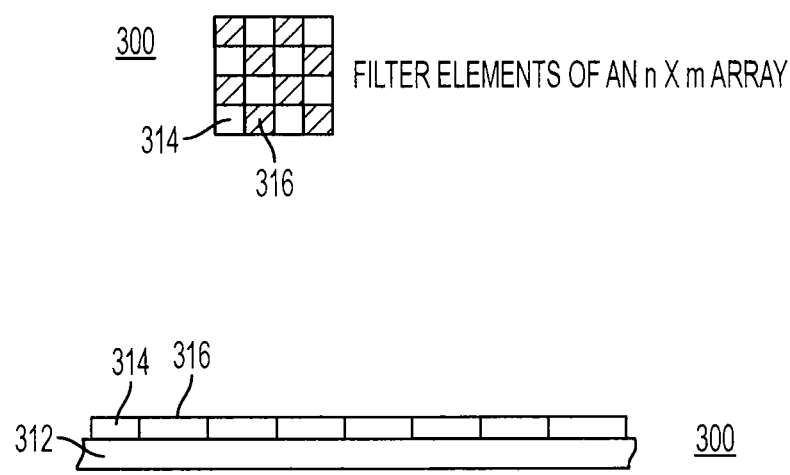
FIG. 7 is a top view and a sectional view of another exemplary filter array, in accordance with an embodiment of the present invention.

Referring next to FIGS. 5 and 7, there is shown another exemplary embodiment of the present invention for detecting methane. As shown, filter array 300 includes two filter elements, an online filter element 70 and an offline filter element 60. The filter elements may be formed on a transparent substrate, designated as 312, by depositing dielectric coating layers designed to form a transmission response curve coinciding with a target's spectroscopic peaks 210 for the online 190 wavelength regions, and the target's spectroscopic non-absorbing regions 212 for the offline 200 wavelength regions. The two filter elements are shown in FIG. 7 as layers 314 alternating with layers 316. The layers 314 transmit an online wavelength for methane and layer 316 transmits an offline wavelength for methane.

One or more lasers, shown as transmitting wavelength 220 in FIG. 5 may be used to illuminate the target. It will be appreciated that transmitting wavelength 220 is sufficiently broad to cover one online wavelength 210 of methane and one adjacent offline wavelength 200 of methane. If the spectral region of a gas of interest is broader than the transmitting wavelength 220, other active illumination sources may be used to cover more of the spectral region of the gas.

The following table lists an exemplary parts list corresponding to the numerical designations in the figures:

| | PARTS LIST |
|---|---|
| 10 | Filter array |
| 20 | Imaging focal plane array |
| 30 | Lens |
| 40 | Imaging object or target gas |
| 50 | Image of the object |
| 60 | Offline filter element 1 |
| 70 | Online filter element 1 |
| 80 | Online filter element 2 |
| 90 | Online filter element 3 |
| 100 | Offline filter element 2 |
| 120 | Data from focal plane array $E_{ij}$ |
| 130 | Offline data from array $Ef_{ij}$ |
| 140 | Online data from array $En_{ij}$ |
| 150 | Interpolated Offline Image $Ef_{ij}$ |
| 160 | Interpolated Online Image $En_{ij}$ |
| 170 | Equation for CPL calculation |
| 180 | Fugitive emissions image CPLij |
| 190 | Example online filter function |
| 200 | Example offline filter function |
| 210 | Example absorption spectrum |
| 220 | Example active illumination spectrum |
| 212 | Example non-absorption spectrum |

What is claimed is:
1. A system for imaging a target comprising:
an imaging array for imaging light from the target,
a filter array, disposed in front of the imaging array, for filtering received light from the target and transmitting the received light to the imaging array,
wherein the received light includes at least one online wavelength corresponding to a wavelength absorbed by the target, and at least one offline wavelength corresponding to a wavelength not absorbed by the target, and the filter array is configured to separate the at least one online wavelength from the at least one offline wavelength, wherein the filter array includes a silicon etalon with an anti-reflective coating deposited in a periodic pattern, and the periodic pattern corresponds to a wavelength spacing between methane absorption features forming the at least one online wavelength.

2. The system of claim 1 wherein
the target includes a species of gas having an absorption wavelength corresponding to the online wavelength and a nonabsorption wavelength corresponding to the offline wavelength.

3. The system of claim 1 including
a processor for receiving the at least one online wavelength and the at least one offline wavelength from the filter array, and
the processor configured to generate corresponding online data and offline data.

4. The system of claim 3 wherein
the online data and offline data are generated from pixel intensities located in at least one sub-array of the imaging array.

5. The system of claim 4 wherein
the processor is configured to interpolate among pixel intensities of the online and offline data generated from the at least one sub-array of the imaging array.

6. The system of claim 3 wherein
the processor is configured to calculate a path integrated concentration of the target, defined as a concentration path length (CPL) of a gas emission from the target.

7. The system of claim 1 wherein
the target includes a species of gas, and
the received light includes two online wavelengths corresponding to two wavelengths absorbed by the species of gas,
the received light includes one offline wavelength corresponding to the one wavelength not absorbed by the species of gas, and
the two online and one offline wavelengths are different from each other.

8. The system of claim 1 wherein
the target includes a species of gas, and
the received light includes one online wavelength corresponding to the one wavelength absorbed by the species of gas,
the received light includes two offline wavelengths corresponding to two wavelengths not absorbed by the species of gas, and
the one online and two offline wavelengths are different from each other.

9. The system of claim 1 wherein
the filter array includes a transparent substrate having dielectric coating layers deposited thereon, and
the dielectric coating layers form a transmission response curve coinciding with the at least one online and the at least one offline wavelengths.

\* \* \* \* \*